United States Patent [19]

Terry

[11] Patent Number: 4,535,082

[45] Date of Patent: Aug. 13, 1985

[54] COMBINING AN ANIONIC BLOCKING AGENT WITH DYPHYLLINE

[75] Inventor: Erwin N. Terry, Montreal, Canada

[73] Assignee: Byk Gulden Lomberg Chemische Fabrik GmbH, Fed. Rep. of Germany

[21] Appl. No.: 214,681

[22] Filed: Dec. 9, 1980

[51] Int. Cl.$^3$ .......................................... A61K 31/465
[52] U.S. Cl. ................................. 514/264; 514/562
[58] Field of Search ................................. 426/253, 319

[56] References Cited

U.S. PATENT DOCUMENTS 4,348,397 9/1982 May et al. .

OTHER PUBLICATIONS

Goodman & Gilman-The Pharmacological Basis of Therapeutics (Textbook), 6th ed., 1980, pp. 929-932.
Cunningham, R. F., et al., "Clinical Pharmacokinetics of Probenecid", *Clinical Pharmacokinetics*, 6:135-151, (1981).
Simons, K. J., and Simons, F. E. R., *J. Pharm. Sci.*, 68, 1327-1328, Oct. 1979.
Research Communications in Chemical Pathology and Pharmacology, vol. 23, No. 3, 523-531, Mar. 1979.
Giscion, L. G., Ayres, J. W. & Ewing, G. H., *Am. J. Hosp. Pharm.*, vol. 36, 1179-1184, Sep. 1979.

*Primary Examiner*—Leonard Schenkman
*Attorney, Agent, or Firm*—Berman, Aisenberg & Platt

[57] ABSTRACT

The potential of dyphylline as a bronchodilator is severely limited by its short half-life. By administering an anionic blocker prior to or concurrently with dyphylline, this shortcoming is overcome, and effective plasma levels can be maintained for as long as eight hours.

18 Claims, No Drawings

COMBINING AN ANIONIC BLOCKING AGENT WITH DYPHYLLINE

TECHNICAL FIELD

The effective utility of dyphylline (D) as a bronchodilator has been materially improved by administration substantially concurrently with probenecid (P).

BACKGROUND

Dyphylline, 7-(2,3-dihydroxypropyl)-3,7-dihydro-1,3-dimethyl-1H-purine-2,6-dione or 7-(2,3-dihydroxypropyl)-theophylline, is described in U.S. Pat. No. 2,575,344. It is a smooth muscle relaxant. The Physician's Desk Reference (PDR), 34th edition, p. 638, lists several pharmaceutical preparations thereof which are said to exert the general pharmacologic actions of theophylline and of aminophyllin, i.e. bronchodilating, myocardial stimulating, diuretic, and coronary, pulmonary, and renal vessels vasodilating actions, of which the bronchodilator activity is the most important in human therapy. The compound is highly soluble, is readily absorbed and well tolerated upon oral administration as well as uniquely suitable for intramuscular injection. In the latter method of administration dyphylline has been shown to be superior to aminophyllin and to theophylline. Another significant advantage to dyphylline is the fact that it has a low incidence of causing gastric irritation.

Probenecid 4-[(dipropylamino)sulfamyl]benzoic acid or p-(dipropylsulfamoyl)benzoic acid, is described in U.S. Pat. No. 2,608,507. It is an uricosuric agent and a renal tubular blocking agent for antibiotics. In particular, P is known to inhibit the tubular secretion of penicillin and thus to elevate penicillin plasma levels. For the latter reason P is widely used as an adjuvant in penicillin therapy, not only with respect to natural penicillin G but also with respect to a large number of semi-synthetic penicillins, such as ampicillin, methicillin, oxacillin, cloxacillin, or nafcillin. P is also used as an adjuvant in cephalosporin therapy.

The pharmacologic actions of D have been studied by P. V. Maney et al. (*J. Amer. Pharm. Assoc.*, Sci. Ed., 35:266, 1966) and J. D. McColl et al. (*J. Pharmacol. Exper. Therap.*, 116:343, 1956). The bronchodilator activity appears to be the most important, and D is most commonly used for the treatment of bronchial asthma and of reversible bronchospasms associated with chronic bronchitis and emphysema; see previously cited PDR, pp. 638 and 639. The only drawback of D would seem to be its short half-life (cf. B. Isaksson et al., *Acta Med. Scand.*, 171:33, 1962, and F. E. R. Simons et al., *J. All. Clin. Immunol.*, 56:347, 1975), which necessitates frequent administration of repeated doses of the drug (cf. K. J. Simons et al., *J. Clin. Pharmacol.*, 17:237, 1977). Contrary to closely related xanthine derivatives, such as caffeine or theophylline, which are all metabolized, dyphylline is substantially not metabolized and is excreted in the urine in unchanged form (cf. L. G. Giscion et al., *Am J. Hosp. Pharm.*, 36:1179, 1979). It has recently been shown that the plasma half-life of D (following oral administration) is 1.8±0.2 hours, with 83±5 percent of the administered dose being recovered unchanged in the urine within 24 hours (cf. K. J. Simons et al., *J. Pharm. Sci.*, 68:1327, 1979).

The pharmacology of P has been extensively studied, in particular its uricosuric activity [cf. A. B. Gutman et al., *Transactions of the Association of American Physicians*, 64:279 to 288 (1951); A. B. Gutman, *Advances in Pharmacology*, 4:91 to 142 (1966); J. H. Talbott et al., "Gout and Uric Acid Metabolism", pp. 225 to 230, Stratton Intercontinental Medical Book Corporation, New York, 1976; V. J. Zarro, "Pharmacology of Gout", in Lowenthal and Major (Ed), "Clinical Therapeutics", pp. 343 to 346, Grune and Stratton, New York, 1978], its effect on penicillin excretion and its effects as an inhibitor of active transport of catecholamines and precursors thereof in the brain.

The "Physicians' Desk Reference" (PDR), 31st Edition, 1977, reflects marketed dosage forms and other products for:

D-
  tablets, liquid and long-acting tablets (p. 610)
  tablets (p. 744)
  tablets, elixir, ampuls (pp. 925 and 926)
  injection, tablets, elixir (pp. 1010 and 1011)
  capsules, liquid (p. 1381)
  tablet, oral liquid (p. 1382)

P-
  oral suspension (p. 660)
  tablets (pp. 1067 and 1068)
  capsules (p. 1539)
  tablets (p. 1754)
  tablets (p. 1757)

Treatment with and use of D are well established, as are suitable dosages for administration of P.

SUMMARY OF THE INVENTION

The present invention relates to a method of treating bronchial asthma and related conditions, such as reversible bronchospasms associated with chronic bronchitis and emphysema, and to compositions useful in the treatment of such pathological conditions. More specifically, this invention relates to a method of treating bronchial asthma and related conditions in humans which comprises substantially simultaneous administration of D and of an effective anionic blocking agent, such as P, to patient suffering from the noted conditions, and to compositions containing effective doses of both of these compounds.

This invention is based on the discovery that substantially simultaneous administration of D and P, preferably in a single composition containing effective amounts of both compounds, significantly increases the plasma half-life of D and inhibits its active transport and excretion by the kidney. "Effective amounts" means amounts or doses of D which prevent, inhibit or alleviate bronchial constriction, such as that found in acute bronchial asthma or in reversible bronchospasms associated with chronic bronchitis or emphysema, and amounts or doses of P which cause a significant increase in the plasma half-life of D and which inhibit the active transport of the latter compound and its excretion by the kidney.

The major advantages of this invention over presently existing forms of treatment of bronchial asthma and related conditions which are due to bronchial constriction are as follows:

Aminophyllin, which has for a long time been regarded as the drug of choice and presently still is the most widely used drug in this field, possesses a number of undesirable gastro-intestinal, central nervous system, cardiovascular, respiratory and renal side effects which are either not presented at all by D, or presented with a significantly diminished incidence. For example, aminophyllin increases the volume and acidity of gastric secretions and is contraindicated in patients with active peptic ulcer disease, while D only rarely exhibits gastrointestinal side effects. The CNS-stimulating effects of aminophyllin are more pronounced and more dangerous than those of D. Respiratory side effects, which are fairly common with aminophyllin, appear to be encountered only very rarely or not at all in D therapy. Moreover, intramuscular injections of aminophyllin are known to be painful, while D is particularly well tolerated when given by this route of administration.

The method of treatment of this invention, by increasing the plasma half-life of D and thus reducing the necessity of frequent administration of repeated doses of the drug, provides the added advantage of increased safety for the patient.

P has been administered in conjunction with antibiotics, analgesics, antiarthritics, uricosurics, diuretics and other drugs, such as allopurinol, heparin, methotrexate and sulfonylureas, but its influence on purine derivatives, e.g. xanthine derivatives, such as theophylline or aminohyllin, has apparently not been investigated. In view of the fact that methyl xanthine derivatives, such as theophylline, aminophyllin and caffeine, are extensively metabolized before being excreted, while D is not metabolized and is substantially excreted in unchanged form, it is both unexpected and surprising that administration of P with D, preferably in a composition or dosage form containing effective amounts of both drugs, increases the plasma half-life of D.

The short plasma half-life of D has also led to attempts to produce a long-acting formulation. One such long-acting dosage form of D is described in the previously-cited PDR, pp. 638 to 639. The bioavailability of D from a long-acting formulation thereof was investigated by Simons (Simons, K. J., Simons, F. E. R., & Bierman, C. W., *J. Clin. Pharmacol.*, 17:237, 1977) and found to be disappointing; in vitro experiments only 52.5×1.9 percent of the D initially present in the long-acting dosage form were released within 4 hours, and only 78 percent within 8 hours. Since absorption in vivo appears to be completed within 5 hours, the limited in vitro release may have been the cause for reduced in vivo bioavailability of the aforesaid sustained release form, amounting to only 67.8 percent (36.8–86.0%) of that of conventional tablets. In contradistinction thereto the compositions of this invention provide high plasma levels of D immediately following administration and maintain plasma levels of D at significantly higher values and for significantly longer periods of time than observed with D alone or with presently existing long-acting dosage forms thereof.

DETAILS

P sufficiently increases the half-life of D to produce a substantial maintenance medication for those subject to asthmatic attacks and to reduce or prevent bronchospasms in allied conditions, such as chronic bronchitis and emphysema. The P is administered either immediately prior to or concurrently with the D for best results; administration of P subsequent to that of D is less effective but is still a material improvement (if administered promptly after) over administration of D alone.

Both P and D are known drugs. Their dosage forms are conventionally made. The drugs are compounded into single formulations in the same manner that they were previously formulated into their individual compositions and resulting dosage forms.

Combined administration of these two drugs is effected enterally or parenterally. Although each drug can be administered by a different mode of administration at approximately the same time, it is advantageous to use the same mode of administration for both and even to incorporate both in a single dosage form.

When both P and D are incorporated in an oral dosage form, both are admixed in a single (otherwise conventional) tabletting composition or they are conventionally incorporated in different layers of a tablet. The same alternatives are available in capsule compositions and time-delay capsule formulations. The subject disclosure is not directed to specific dosage forms or modes of administration; both of these aspects are regarded as conventional in respects other than the concurrent or nearly concurrent administration of both P and D. However, conventionally-prepared time-delay formulations and dosage forms are particularly advantageous and provide a significant improvement over other dosage forms.

For each 2 to 10 mg of D administered, from 0.5 to 10 (preferably from 1.5 to 10) mg of P is administered. Illustrative daily doses range from about 8.5 to about 43 mg/kg of body weight of D and from about 2 to about 30 mg/kg of body weight of P. Typical unit dosages for an adult patient are from 200 to 1000 mg, preferably 300 to 500 mg, of D (administered every eight hours) and from 50 to 700 mg, preferably 80 to 150 mg, of P administered at the same frequency. The effective duration of treatment with D is about eight hours when administered concurrently with or following administration of P.

Studies on the excretory transport of D and its inhibition by P, using the Sperber chicken model (Sperber, I., *Lantbrukshoegsk. Ann.*, 15:317, 1948; Lindahl, K., and Sperber, I., *Acta Physiol. Scand.*, 42:166, 1958), show that:

1. D is actively excreted by the renal tubule of the chicken at a rate of one-half that of a compound (tetraethylammonium) completely excreted in one pass through the kidney, and
2. P dose-dependently inhibits this active excretion of D. Infusion of 1.8 μmol/min. inhibits excretion of 100 μg/min. of D by 60 percent. This inhibition increases with increasing infusion rates of P to 83 percent at an infusion rate of 16 μmol/min. of P.

This model is made possible by the existence of a separate renal, portal circulation in the chicken, accessible through a leg vein. Laying hens (Rhode Island White/Rhode Island Red cross) weighing between 2 to 3 kg are used. The unanesthetized animals are hydrated with 50 ml of water at the beginning and every 30 to 40 minutes throughout the experiment. Urine is collected separately from each ureter, and the excretion per minute (Exc) of substrate from the infused and control kidney are measured. Substrate is infused into a saphenous vein in the leg. Any such infused substrate goes to the renal portal circulation and bathes the renal tubules. Substrate secreted by the renal tubules appears in the urine collected from the ureter of the ipsilateral kidney (relative to the infused saphenous vein) in excess to that collected from the contralateral kidney.

The excess excreted from the infused kidney can be expressed as
ti APPARENT TUBULAR EXCRETION FRACTION (ATEF)

which is calculated as: $(Exc_{infused}-Exc_{control})$/amount infused per min. expressed as a percentage. To document the amount of infusion reaching the infused kidney, a compound extracted completely by the kidney (such as tetraethylammonium orp-aminohippuric acid) is infused simultaneously.

The ratio $$ATEF_{substrate}/ATEF$$

compound completely extracted by tubules is referred to as

TRANSPORT EFFICIENCY (TE)

and relates the amount of substrate transported by the renal tubule to that which reached the kidney. The maximal TE that could result from diffusion from peritubular blood into tubular fluid, based on the relation of glomerular filtration rate to renal plasma flow rate, is 0.08. Thus, TE value significantly in excess of 0.08 is considered to indicate the effect of renal tubular transport. A number of substrates have been demonstrated to be excreted by the proximal tubule in mammals (including man) and birds by the organic anionic or organic-cation-transport system. (Rennick, B., & Quebbeman, A. J., in "Renal Pharmacology", Eds. J. W. Fisher & E. J. Cafruny, Appleton-Century-Crofts, N.Y., 1971, p. 67). P is a selective inhibitor of the anion transport system. It was developed as a penicillin secretion inhibitor (Beyer, K. H., Russo, H. F., Tillson, E. K., Miller, A. K., Verwey, W. F., & Gass, S. R., *Amer. J. Physiol.*, 166:1951). P is now also established as a research-tool in the identification of the anion transport system, in the kidney as well as in processes by which acidic metabolites are removed from the brain and the cerebro spinal fluid, both processes being similar (Despopoulos, A., & Weissbach, H., *Amer. J. Physiol.*, 189:548, 1957, Ashcroft, G. W., Dow, R. C., & Moir, A. T. B., *J. Physiol.*, 199:397, 1968). P was found to block tubular transport of 5-hydroxyindolacetic acid (5-HIAA) infused into the renal portal system of the Sperber Model (Hakim, R., Watrous, W. M., & Fujimoto, J. M., *J. Pharmacol. Exp. Therap.*, 175:749, 1970) to the same extent as transport from the CSF in man (Tamarkin, N. R., Goodwin, F. K., & Axelrod, J., *Life Sciences*, 9:1397, 1970, Roos, B. E. & Sjostrom, R., *Pharmacologia clinical*, 1:153, 1969).

Prior to this invention there was no reason to suspect that the half-life of D could be significantly increased or how such increase might be effected. No compound was previously known to be a renal tubular blocking agent for D, nor was there any evidence that such a blocking agent even existed.

EXAMPLE

Tablets containing 400 mg of dyphylline and 100 mg of probenecid:

2.08 kg of polyvinylpyrrolidone of an average molecular weight of 90,000 and 2.08 kg of ethyl cellulose are dissolved in 40.00 l of denatured ethanol. In a rotating dragee-making vessel 4.62 kg of sugar spherulets with an average diameter of 0.8 mm are moistened thoroughly with 400 ml of this solution. Following this 400 g of finely pulverized dyphylline are applied to the moistened spherulets. After drying with air from a blower the spherulets are again moistened with 400 ml of the ethanolic polyvinylpyrrolidone/ethyl cellulose solution and further 400 g of dyphylline are applied. The operation is repeated until the whole amount of dyphylline has been applied.

The resulting pellets are sprayed in a fluidized bed apparatus with a solution of 0.906 kg of ethylcellulose, 0.210 kg of stearic acid, 0.326 kg of methacrylic acid-methacrylic acid ester copolymerisate with an acid number of 292 (Eudragit ®L), 0.386 kg of methacrylic acid-methacrylic acid ester copolymerisate with an acid number 178 (Eudragit ®S) and 0.204 kg of triacetin. 50.8 kg of dyphylline retard pellets are obtained.

10.0 kg of probenecid, 9 kg of polyvinylpyrrolidone of an average molecular weight of 25,000, 8.0 kg of polymethacrylic acid (Carbopol ®934), 1.50 kg of microcrystalline cellulose, 0.30 kg of highly disperse silicic acid (Aerosil ®) and 0.20 kg of magnesium stearate are mixed and prepressed on a tabletting machine and granulated through a sieve of 1.2 mm mesh width. The obtained granulated material is mixed and pressed together with 50.8 kg of dyphylline retard pellets to form 100,000 tablets weighing 800 mg.

The invention and its advantages are readily apparent from the preceding description. Various changes may be made in the process, method of use, compositions and dosage forms without departing from the spirit or scope of the invention or sacrificing its material advantages. That which is hereinbefore described and illustrated merely reflects preferred embodiments.

What is claimed is:

1. A process for increasing the half-life of dyphylline administered to a human which comprises prior or concurrent administration of an effective amount of probenecid.

2. A process according to claim 1 which comprises administering from 1.5 to 10 milligrams of probenecid for each 2 to 10 milligrams of dyphylline.

3. A process according to claim 1 which comprises administering dyphylline medication to a human subject to asthmatic attacks or to a human to reduce or prevent bronchospasm.

4. A process according to claim 1 for treating a human afflicted with bronchial asthma which comprises administering to the human an effective dose of dyphylline.

5. A process according to claim 4 which comprises administering an effective dose of dyphylline to the human every eight hours.

6. A process according to claim 1 which comprises administering a dose of from 200 to 1000 milligrams of dyphylline to the human.

7. A pharmaceutical composition suitable for treating a human afflicted with bronchial asthma and which comprises dyphylline and probenecid, the amount of probenecid, per effective dose of dyphylline being sufficient to increase the half-life of the dyphylline significantly.

8. A pharmaceutical composition according to claim 7 wherein dyphylline and probenecid are in a suitable solid or liquid carrier.

9. A pharmaceutical composition according to claim 7 comprising from 150 to 1000 milligrams of probenecid for each 200 to 1000 milligrams of dyphylline.

10. A pharmaceutical unit dosage form comprising from 200 to 1000 milligrams of dyphylline and from 50 to 1000 milligrams of probenecid.

11. A method of enhancing the retention of dyphylline in the human system into which it is administered which comprises administering a retentively effective amount of probenecid to said system at substantially the time of administration of the dyphylline, wherein the amount of dyphylline administered is between about 8.5 and about 43 milligrams per kilogram of body weight and the amount of probenecid administered is between about 2 and about 30 milligrams per kilogram of body weight.

12. A method according to claim 11 wherein the probenecid is administered prior to the administration of the dyphylline.

13. A method according to claim 11 wherein the probenecid is administered substantially simultaneously with the dyphylline.

14. A method according to claim 11 wherein the dyphylline and probenecid are each administered at intervals of about 8 hours.

15. A method of enhancing the bronchodilatory action of dyphylline which comprises treating a human subject in need of treatment with a bronchodilator with dyphylline in the presence of a sufficient amount of probenecid to increase the retention of dyphylline in the system of said subject, wherein the amount of dyphylline administered is between about 8.5 and about 43 milligrams per kilogram of body weight and the amount of probenecid administered is between about 2 and about 30 milligrams per kilogram of body weight.

16. A bronchodilatorily active composition comprising dyphylline and a sufficient amount of probenecid to substantially increase the retention of dyphylline in the human system, wherein the ratio of dyphylline to probenecid lies between 1:1 and 4:1, by weight.

17. A composition in accordance with claim 16 comprising between 200 and 1,000 miligrams of dyphylline and between 50 and 700 milligrams of probenecid per unit dose.

18. A composition in accordance with claim 16 wherein the ratio of dyphylline to probenecid lies between 1:5 and 20:1.

* * * * *